US00PP19571P2

(12) United States Plant Patent
Zary

(10) Patent No.: US PP19,571 P2
(45) Date of Patent: Dec. 16, 2008

(54) FLORIBUNDA ROSE PLANT NAMED 'JACFRAIN'

(50) Latin Name: *Rosa hybrida*
Varietal Denomination: JACfrain

(75) Inventor: Keith W. Zary, Thousand Oaks, CA (US)

(73) Assignee: Jackson & Perkins Wholesale, Inc., Hodges, SC (US)

( * ) Notice: Subject to any disclaimer, the term of this patent is extended or adjusted under 35 U.S.C. 154(b) by 0 days.

(21) Appl. No.: 11/998,693

(22) Filed: Nov. 29, 2007

(51) Int. Cl.
*A01H 5/00* (2006.01)

(52) U.S. Cl. ..... Plt./145

(58) Field of Classification Search ..... Plt./145
See application file for complete search history.

*Primary Examiner*—Kent L. Bell
*Assistant Examiner*—Georgia Helmer
(74) *Attorney, Agent, or Firm*—Klarquist Sparkman LLP

(57) ABSTRACT

Floribunda rose plant with flowers having a sweet musk fragrance; vigorous upright growth, well branched; large, multicolored blooms; disease resistant foliage; petals that drop cleanly and high centered flowers.

1 Drawing Sheet

Genus and Species: *Rosa hybrida.*
Variety Denomination: 'JACfrain'.

ORIGIN OF THE INVENTION

The present invention relates to a new and distinct variety of a floribunda rose plant named 'JACfrain' which was originated by me by crossing the variety 'AROfres' (not patented, seed parent), with the variety 'MACivy' (U.S. Plant Pat. No. 8,362, pollen parent).

BACKGROUND OF THE INVENTION

The primary objective of this breeding was to produce a new floribunda rose variety having the disease resistant foliage, large flower size, high-centered form and ability to drop its petals cleanly of the female parent combined with the vigorous upright growth and sweet musk fragrance of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Sweet musk fragrance.
2. Vigorous upright growth, well branched.
3. Large, multicolored blooms.
4. Disease resistant foliage.
5. Petals that drop cleanly.
6. High centered flowers.

Asexual reproduction of this new variety by cuttings, as performed at Wasco, Calif., shows that the foregoing characteristics and distinctions come true to form and are established and transmitted through succeeding propagations.

COMPARISON WITH PARENTS

'JACfrain' differs from 'AROfres' in plant habit (typically 120 cm tall for 'JACfrain' versus 80 cm for 'AROfres') and flower color (yellow, pink, orange blend for 'JACfrain' versus yellow for 'AROfres'). 'JACfrain' differs from 'MACivy' in flower color (yellow, pink, orange, blend for 'JACfrain' versus apricot copper for 'MACivy').

COMPARISON WITH SIMILAR VARIETY

Although it is difficult to find a comparison variety, 'JACtorse' (U.S. Plant Pat. No. 12,129) is an example variety. 'JACfrain' differs from 'JACtorse' in flower color (yellow, pink, orange blend for 'JACfrain' versus deep pink with creamy reverse for 'JACtorse') and in fragrance (apple for 'JACtrose' versus musk for 'JACfrain').

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—'AROfres' (yellow, floribunda) (not patented).
*Pollen parent.*—'MACivy' (U.S. Plant Pat. No. 8,362).

FLOWER

Observations made from January 2006 to October 2007, from plants four years at completion of observations, growing in a garden environment at Somis, Calif.

Blooming habit: Continuous.
Bud:
*Size.*—About 3.5–4 cm long and 2–2.5 cm in diameter when the petals start to unfurl.

*Form.*—The bud form is pointed ovoid.

*Color.*—When sepals first divide, bud color is mainly Yellow Group 9B edged with Red Group 43C. When half brown, the upper sides of the petals are Red Group 43B at apex, graduating to Yellow Group 9B at base. The lower sides of the petals are mostly Yellow Group 9B tipped with Red Group 43C at the apex.

*Sepals.*—Color: Upper surface: Predominantly Yellow-Green Group 144C with Green Group 141A and Greyed-Purple Group 183A on outer tip. Lower surface: Green Group 143B with Greyed-Purple Group 183A on tip. Length: 25–35 mm. Width: 9–12 mm. Shape: Subulate. Surface: Upper: Hoary. Lower: Smooth with occasional glands (average 8 per sepal). There are three lightly appended sepals. There are two unappendaged sepals with hairy edges.

*Receptacle.*—Color: Yellow-Green Group 144B. Shape: Funnel. Size: Medium, about 6–8 mm long× 8–10 mm in width. Surface: Smooth, with a few tiny hairs.

*Peduncle.*—Length: Long, averaging about 10–15 cm. Surface: Smooth with small hairs. Color: Yellow-Green Group 144B. Strength: Stiff, erect.

Bloom:

*Size.*—Medium: Average open diameter is about 8–12 cm.

*Borne.*—Singly and in clusters of 3–5 blooms having a pyramidal shape.

*Stems.*—Strength: Strong. Average length is about 40–50 cm with a diameter of 4–6 mm.

*Form.*—When first open: High centered. Permanence: All petals curl with age, quill fashion.

*Petalage.*—Number of petals under normal conditions: 20–25.

*Color.*—The upper sides of the petals are Red Group 43B at apex, graduating to Yellow Group 9B at base. The reverse sides of the petals are mostly Yellow Group 9B edged in Red Group 40D. The base of the petals has Yellow Group 9B. The major color on the upper sides is Red Group 43B and Yellow Group 9B.

*Discoloration.*—The general tonality at the end of the first day: No change. At the end of the third day: Red Group 43B changes to Red Group 47C. By day 5, Red Group 47C changes to Red Group 52B.

*Fragrance.*—Moderate, musk.

Petals:

*Thickness.*—Thick.

*Surface texture.*—Smooth.

*Shape.*—Obovate.

*Margin.*—Entire.

*Apex shape.*—Cuspidate.

*Base shape.*—Rounded.

*Form.*—Moderately quilled.

*Arrangement.*—Imbricated.

*Petaloids.*—Number: From 4 to 8.

*Persistence.*—Petals drop off cleanly before drying.

*Lastingness.*—On the plant: Fair (about 5–6 days). As a cut flower: Fair (about 6–7 days).

Reproductive parts:

*Stamens.*—Number: 60–65. Length: 8 mm. Anthers: Length: 3 mm. Color: Yellow-Orange Group 15C. Arrangement: Regular around styles, mixed with petaloids. Filaments: Color: Yellow-Orange Group 15B. Length: 5–6 mm. Pollen: Color: Greyed-Orange Group N167B.

*Pistils.*—Number: 35–40. Length: 6–7 mm. Styles: Color: Greyed-Purple Group 187D. Length: 5–6 mm. Stigmas: Color: Greyed-Yellow Group 161D. Length: 1 mm. Hips: None observed.

PLANT

*Form.*—Bush.

*Growth.*—Very vigorous, upright, branching.

*Age to maturity.*—Two years.

*Mature plant.*—Height: 120 cm. Width: 80 cm.

*Rootstock.*—Own root.

Foliage: Number of leaflets on normal mid-stem leaves; 5 or 7.

*Size.*—Large. About 120 mm long×80 mm wide.

*Quantity.*—Abundant.

*Color.*—New foliage: Upper side: Greyed-Purple Group 183A. Lower side: Greyed-Purple Group 183C. Old foliage: Upper side: Green Group 139A. Lower side: Yellow-Green Group 147B.

Leaflets:

*Size.*—About 40 mm long×33 mm wide.

*Shape.*—Oval.

*Base shape.*—Rounded.

*Apex shape.*—Acuminate.

*Texture.*—Leathery.

*Edge.*—Serrated.

*Serrations.*—Single.

*Petiole.*—Color: Yellow-Green Group 147C, sometimes with an overlay of Greyed-Purple 183D.

*Petiole rachis.*—Color: Yellow-Green Group 147C. Underside: Rough with prickles and glands.

*Auricles.*—Not observed.

*Stipules.*—Length: 15 mm, serrated.

*Disease resistance.*—Resistant to rust and mildew, susceptible to blackspot under normal growing conditions.

*Pest resistance.*—None observed.

*Vein color.*—Yellow-Green Group 147C.

*Venation pattern.*—Reticulate.

Wood:

*New wood.*—Color: Greyed-Purple Group 183C quickly turning to Yellow-Green Group 146C. Bark: Smooth.

*Old wood.*—Color: Yellow-Green Group 146A often overlain with Greyed-Purple Group 183D when exposed to full sun. Bark: Smooth.

Prickles:

*Quantity.*—Ordinary, on main canes from base: 13–15 per 15 cm of wood. Ordinary, on laterals from main canes: 13–15 per 15 cm of wood.

*Form.*—Hooked downward.

*Length.*—8–10 mm.

*Color when young.*—Greyed-Purple Group 183D.

*Color when mature.*—Greyed-Orange Group 177B.

Small prickles:

*Quantity.*—On main stalks: None. On laterals: None.

Winter hardiness: Hardy to zone 5.

I claim:

1. A new and distinct variety of floribunda rose plant, substantially as herein shown and described, characterized particularly by a sweet musk fragrance; vigorous upright growth, well branched; large, multicolored blooms; disease resistant foliage; petals that drop cleanly and high centered flowers.

* * * * *

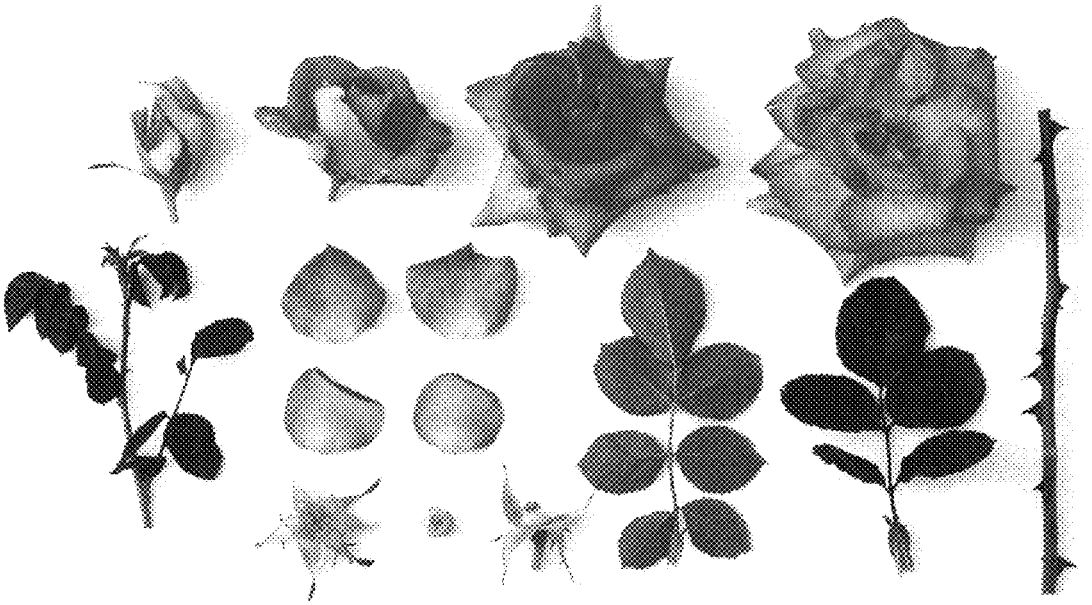
JACfrain